United States Patent [19]

Moon

[11] 4,006,132

[45] Feb. 1, 1977

[54] 1'-FORMYL-1'-HALOBENZENEAZOMETHANE COMPOUNDS HAVING HERBICIDAL ACTIVITY

[75] Inventor: Malcolm W. Moon, Kalamazoo, Mich.

[73] Assignee: The Upjohn Company, Kalamazoo, Mich.

[22] Filed: Nov. 14, 1975

[21] Appl. No.: 631,865

Related U.S. Application Data

[60] Continuation of Ser. No. 468,768, May 10, 1974, abandoned, which is a division of Ser. No. 138,338, April 28, 1971, Pat. No. 3,830,642.

[52] U.S. Cl. .............................. 260/192; 260/193; 260/544 R; 260/566 B; 260/543 A
[51] Int. Cl.² .................. A01N 9/24; C07C 107/04
[58] Field of Search ........................... 260/192, 193

[56] References Cited

UNITED STATES PATENTS

| | | | |
|---|---|---|---|
| 3,150,151 | 9/1964 | Urbschat et al. | 260/326.5 |
| 3,282,912 | 11/1966 | Benzing | 260/158 |
| 3,491,084 | 1/1970 | Huenig et al. | 260/192 |
| 3,715,435 | 2/1973 | Harnish et al. | 424/226 |
| 3,786,131 | 1/1974 | Buchel et al. | 424/304 |

Primary Examiner—Floyd D. Higel
Attorney, Agent, or Firm—John J. Killinger; Roman Saliwanchik

[57] ABSTRACT

Compounds of the formula:

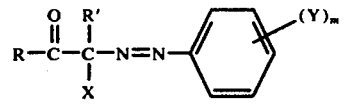

wherein R is alkyl of from 1 to 8 carbon atoms, inclusive; alkoxy of from 1 to 8 carbon atoms, inclusive; haloalkoxy of from 1 to 8 carbon atoms, inclusive; cycloalkyl of from 3 to 8 carbon atoms, inclusive; cycloalkoxy of from 3 to 8 carbon atoms, inclusive; or haloalkyl of from 1 to 8 carbon atoms, inclusive; R' is lower-alkyl of from 1 to 8 carbon atoms, inclusive, phenyl, cycloalkyl of from 3 to 8 carbon atoms, inclusive; or X; X is bromine, chlorine, or fluorine; $m$ is an integer 0 through 5, inclusive, and Y is (independently when $m$ is more than 1) halogen, lower-alkyl of from 1 to 4 carbon atoms, inclusive, lower-alkoxy of from 1 to 4 carbon atoms, inclusive, or halolower-alkyl of from 1 to 4 carbon atoms, inclusive; providing however, that $m$ is 2 to 5 whenever R' is X, and that the sum of the carbon atoms in substituents $(Y)_m$ is not more than 15.

41 Claims, No Drawings

1'-FORMYL-1'-HALOBENZENEAZOMETHANE COMPOUNDS HAVING HERBICIDAL ACTIVITY

CROSS REFERENCE TO RELATED APPLICATIONS

This application is a continuation of application Ser. No. 468,768, filed May 10, 1974, now abandoned which in turn is a division of my copending application Ser. No. 138,338, filed Apr. 28, 1971 now U.S. Pat. No. 3,830,642.

STATEMENT OF THE INVENTION

This invention pertains to new organic chemical compounds, to a process for preparing the same, to a new method for controlling weeds, and to new formulations effective for controlling weeds. The invention is more particularly directed to new 1'-formyl-1'-halobenzeneazomethanes, to a new process for preparing the same by halogenation of an appropriate phenylhydrazone, to a new method for controlling weeds with the new 1'-formyl-1'-halobenzeneazomethanes, and to new formulations comprising the 1'-formyl-1'-halobenzeneazomethanes effective for controlling weeds.

SUMMARY OF THE INVENTION

The new 1'-formyl-1'-halobenzeneazomethanes of this invention have the following general structural formula:

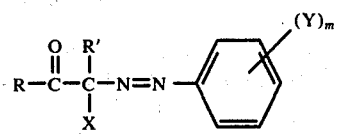

wherein R is alkyl of from 1 to 8 carbon atoms, inclusive; alkoxy of from 1 to 8 carbon atoms, inclusive; cycloalkyl of from 3 to 8 carbon atoms, inclusive; cycloalkoxy of from 3 to 8 carbon atoms, inclusive haloalkyl of from 1 to 8 carbon atoms, inclusive; and haloalkoxy of from 1 to 8 carbon atoms, inclusive; R' is lower-alkyl of from 1 to 8 carbon atoms, inclusive; cycloalkyl of from 3 to 8 carbon atoms, inclusive; phenyl; or X; X is bromine, chlorine, or fluorine; $m$ is an integer 0 through 5, inclusive; and Y is (independently when $m$ is more than 1) halogen, lower-alkyl of from 1 to 4 carbon atoms, inclusive; lower-alkoxy of from 1 to 4 carbon atoms, inclusive, or halolower-alkyl of 1 to 4 carbon atoms, inclusive providing however that $m$ is at least 2 whenever R' is X, and that the sum of the carbon atoms in substituents Y may not be more than 15.

The new 1'-formyl-1'-halobenzeneazomethanes of Formula 1, above, are active against weeds and can be used as herbicides. The compounds kill weed seedlings when applied as a direct contact spray. The compounds are also active against arthropod pests and can be used as pest control agents in situations where phytotoxicity is not a limiting factor. In certain circumstances however, control of insect pests can be achieved at concentrations and in special formulations that minimize or avoid phytotoxic affects.

The new formulations of the invention comprise the new 1'-formyl-1'-halobenzeneazomethanes in solutions, emulsifiable concentrates, suspension in a liquid, flowable creams, wettable powders, other powders (e.g., dusts), granules, and elastomeric pellets, strips, or sheets. More particular details about some of the new formulations are described hereinbelow.

The new 1'-formyl-1'-halobenzeneazomethanes according to Formula I are prepared by halogenation of a corresponding phenylhydrazone. The preferred halogenating agents are elemental chlorine or bromine and the various alkyl hypohalites, e.g., tert.butyl hypochlorite or hypobromite, and trifluoromethyl hypofluorite. When preparing compounds according to Formula I, above, having R' lower-alkyl, cycloalkyl, or phenyl the presence and nature of a Y substituent group is not critical. Thus compounds according to the invention wherein $m$ is zero or 1 (as well as $m = 2-5$) can be prepared.

When preparing the compounds of the invention according to Formula I wherein R' is halogen, there will be some tendency to form the azo compounds with halogen substituents at unsubstituted activated 2,4- and 6-positions in the benzene ring. Thus, for example, pyruvoyl chloride o-tolyl hydrazone reacts with chlorine to give the 4,6-dichloro-o-tolylazo compound of Structure I.

There are other variations in the halogenation procedure that can be used by those skilled in the art to prepare compounds according to Formula I. Thus strong solvents, e.g., acetic acid will promote halogenation.

DETAILED DESCRIPTION OF THE INVENTION

In accordance with Formula I, the variables, R, R', X, Y, and m are defined generally. This structural formula and defined variables contemplate the operable embodiments of this invention. It is expected that, with few exceptions, the various specific compounds of the formula will have the same general biological activities as the specific compounds of the invention that have been prepared and tested.

In general, the variables are to be considered independently, and, for example, the X variable at a position can be chlorine when an X variable at another position can be chlorine, bromine, or fluorine. Similarly, a variable Y can be halogen, e.g., chlorine, while another Y variable can be methyl, halogen, alkoxy, or haloalkyl.

Thus considered, the whole scope of 1'-formyl-1'-halobenzeneazomethanes according to Formula I can be better visualized by consideration of some specific identities of variables. Illustratively, R being "alkyl of from 1 to 8 carbon atoms, inclusive;" includes, for example, methyl, ethyl, propyl, butyl, pentyl, hexyl, heptyl, octyl, and isomeric forms thereof, e.g., isopropyl.

Similarly, R being "alkoxy of from 1 to 8 carbon atoms, inclusive;" includes, for example, methoxy, ethoxy, propoxy, butoxy, pentoxy, hexoxy, heptoxy, octoxy, and isomeric forms thereof, e.g., sec.butoxy and isopropoxy.

Similarly, R being "cycloalkyl of from 3 to 8 carbon atoms, inclusive;" includes for example, cyclopropyl, cyclobutyl, cyclopentyl, cyclohexyl, cycloheptyl, cyclooctyl, and 2,4-dimethylcyclohexyl, and the like.

Similarly, R being "cycloalkoxy of from 3 to 8 carbon atoms, inclusive;" includes, for example, cyclopropyloxy, cyclobutyloxy, cyclopentyloxy, cyclohexyloxy, cycloheptyloxy, cyclooctyloxy, 2,3,4-trimethylcyclopentyloxy, and the like.

Similarly, R being "haloalkyl of from 1 to 8 carbon atoms, inclusive;" includes, for example, chloromethyl, dibromomethyl, and trifluoromethyl; haloethyl, e.g., 2-chloroethyl, 1,2-dichloroethyl, 2-iodoethyl, 2,2,2-trifluoroethyl; halopropyl, e.g., chloro-n-propyl, bromo-n-propyl, iodoisopropyl; halobutyl; and halooctyl.

Similarly, R being "haloalkoxy of from 1 to 8 carbon atoms, inclusive;" includes, for example, fluoromethoxy; haloethyoxy, e.g., 2-chloroethoxy, 1,2-dichloroethoxy, 2-iodoethoxy, 2,2,2-trifloroethoxy; halopropoxy, e.g., chloro-n-propoxy, bromo-n-propoxy, iodoisopropoxy, and halooctoxy.

The reaction of triketone phenylhydrazone with a hypohalite can be illustrated as follows. A 4-R-2,3,4-triketone 3-phenylhydrazone is reacted with the hypohalite, e.g., tert.butyl hypochlorite to produce a 3-chloro-3-phenylazo-4-R-2,4-diketone as an intermediate which is hydrolyzed with an alcohol, e.g., methanol or ethanol to produce the desired R-glyoxyloyl chloride 1-phenylhydrazone.

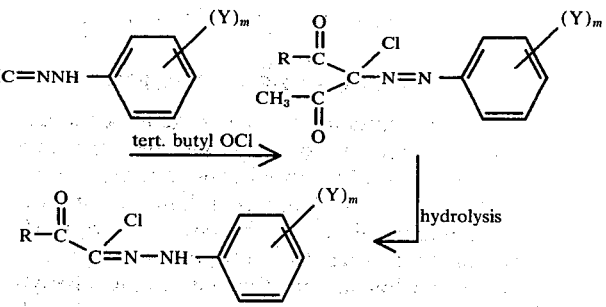

The variable X is identified as the halogens bromine, chlorine, and fluorine. Noting particularly though that the substituent Y as a halogen can be bromine, clorine, fluorine, and iodine.

The variable R' being lower-alkyl, cycloalkyl, or X is consistent with the specific identities set forth above for R and X. And the specific identities of variable Y follow the same scope, the stated carbon atom limitations being observed for Y.

The new 1'-formyl-1'-halobenzeneazomethanes according to Formula I wherein R' is halogen and R is alkyl, cycloalkyl, and haloalkyl are conveniently prepared by vigorous halogenation from corresponding R-glyoxyloyl halide phenylhydrazones of the formula:

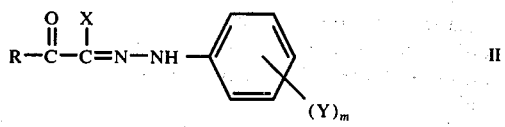

In a most convenient procedure a glyoxyloyl halide phenylhydrazone according to Formula II is reacted with a excess of elemental chlorine to provide 1'-R-formyl-1'-cloro-1'-halobenzeneazomethanes according to the invention. The compounds of the invention prepared in this way will be chlorinated at unsubstituted 2,4 and 6-positions in the benzene ring if the starting R-glyoxyloyl halide phenylhydrazone has reactive sites at these positions. This expected chlorination of the benzene ring will not occur if the starting phenylhydrazone has multiple Y substituents already in the otherwise reactive positions.

The starting R-glyoxyloyl halide 1-phenylhydrazones are prepared by reacting a triketone phenylhydrazone with a lower-alkyl hypohalite or akaline earth metal hypohalite. Any of te various available hypohalites can be used, particularly hypobromites and hypoclorites for preparing the intermediates of this invention. Illustratively, sodium, potassium, and calcium hypohalites can be used. Preferred lower-alkyl hypohalites are tert.butyl hypochlorite and tert.butyl hypobromite. Propyl and ethyl hypohalites can also be used.

wherein R can be any hydrocarbon or halohydrocarbon, advantageously, alkyl, haloalkyl, or cycloalkyl.

The reaction is effected by adding one equivalent (or an excess, if desired) of the chosen hypohalite to an organic solution of a selected triketone phenylhydrazone. Chloroform is a preferred organic solvent although ethanol, benzene, toluene, and carbon tetrachloride can be used.

The alkyl hypohalites are liquids and are soluble in the above organic solvents. The reaction is often exothermic, especially when the phenyl ring is unsubstituted; for example, 2,3,4-pentanetrione 3-phenylhydrazone was chlorinated within minutes using tert.butyl hypochlorite. 2,3,4-Pentanetrione 3-(2,4-dichlorophenyl)hydrazone on the other hand required several hours for chlorination. Accordingly, the reaction mixture can be warmed gently in order to speed the reaction when there are deactivative substituents on the phenylhydrazone ring. The hypohalite reagent is aggressive enough that caution should be used in handling the reactions.

The alkaline earth metal hypohalites are solids and are dissolved in water for addition to the organic solution or triketone phenylhydrazone. The reaction proceeds in the two-phase system with the halogenated phenylazo compound remaining in the organic phase.

The hydrolysis step is advantageously effected with a mild hydrolytic reagent such as methanol or ethanol (preferred) dilute aqueous sodium hydroxide, or morpholine. The intermediate advantageously is separated from the reaction medium by conventional procedures such as removing the organic solvent by evaporation. The residue is then dissolved in methanol or ethanol for hydrolysis. The desired R-glyoxyloyl chloride or bromide 1-phenylhydrazone separates from the alcoholic medium and can be readily recovered by well-known manipulative techniques such as filtration and solvent evaporation.

The 4-R-2,3,4-triketone 3-phenylhydrazone starting compounds in the new process are readily prepared by reacting a 4-R-2,4-diketobutane with a benzene diazonium chloride according to the methods described by Beyer and Claisen, Ber. 21, p. 1702 (1888) and Bulov and Schlotterbeck, Ber. 35, p. 2188 (190).

Various starting compounds according to Formula II are prepared by halogenation of R-glyoxaldehyde 1-phenylhydrazone starting compounds. Illustratively, pyruvaldehyde 1-phenylhydrazone itself can be reacted with elemental bromine, or elemental chlorine to give, e.g., pyruvoyl bromide 1-[(p-bromophenyl)hydrazone], pyruvoyl chloride 1-[(2,4-dichlorophenyl)hydrazone], and pyruvoyl chloride 1-[(p-chlorophenyl)-hydrazone]. Starting pyruvaldehyde 1-phenylhydrazones and pyruvoyl halide 1-(phenylhydrazones) related to those specified are prepared by methods known in the art. A preferred method in accordance with this invention is by halogenation of a pentanetrione phenylhydrazone. The new method described above is one of them. Alternative methods are by direct chlorination or bromination with limited or excess amounts of chlorine or bromine. This method cannot be used when the desired compound requires m equal zero. For example, with limited amounts of chlorine, e.g., 3 to 4 equivalents there is rapid chlorination of, e.g., 2,3,4-pentanetrion 3-phenylhydrazone to give pyruvoyl chloride (2,4-dichlorophenyl)hydrazone and small amounts of chloropyruvoyl chloride (2,4-dichlorophenyl)hydrazone.

When ever larger amounts (e.g., 5 to 10 equivalents) of chlorine are reacted with 2,3,4-pentanetrione 3-phenylhydrazone at about 10° C. there are produced multiple chlorinated products including e.g., pyruvoyl chloride (2,4,6-trichlorophenyl)hydrazone, chloropyruvoyl chloride (2,4,6-trichlorophenyl)hydrazone, dichloropyruvoyl chloride (2,4,6-trichlorophenyl)hydrazone and miscellaneous other chlorinated compounds. This halogenation produce is not recommended for other than halogenated starting compounds according to Formula II.

Otherwise, pyruvoyl chloride phenylhydrazone starting compounds can be prepared by reacting a benzene diazonium chloride with chloroacetone. The benzene diazonium chlorides are prepared from aniline or a substituted aniline by diazotization.

A convenient and efficient method is to react 3-halo-4-R-2,4-diketobutane with a benzene diazonium chloride in aqueous solution. This method is broadly applicable for starting compounds according to this invention.

Pyruvoyl bromide 1-phenylhydrazones are most conveniently prepared by reaction of a pyruvaldehyde phenylhydrazone with bromide. Bromination of 2,3,4-pentanetrione 3-phenylhydrazones gives the bromo- and dibromopyruvoyl bromide phenylhydrazones.

Isolation of the intermediate R-glyoxyloyl halide 1-phenylhydrazones of Formula II is particularly desirable when the 1'-formyl-1'-halobenzeneazomethane to be synthesized has R' and X as different halogens. When R' and X are to be the same halogen it should be noted that a convenient one step synthesis for some of the compounds of this invention is by vigorous halogenation of a 4-R-2,3,4-triketone 3-phenylhydrazone or a pyruvaldehyde phenylhydrazone. In this reaction, compounds of Formula II ae first formed during chlorination but are not isolated.

The starting compounds according to Formula II wherein R is alkoxy, cycloalkoxy, and haloalkoxy are prepared in a similar fashion by esterification of a chloroglyoxyloyl halide 1-(jphenylhydrazone) with any desired alcohol, or by condensing any R-acetoacetate with a benzene diazonium halide as described in Example I followed by halogenation of the thus obtained R-2,3-dioxobutyrate 2-phenylhydrazone.

Starting phenylhydrazones for the process of this invention wherein R and R' are alkyl or cycloalkyl are prepared by condensing an appropriate dione, e.g., butane-2,3-dione, hexane-3,4-dione, or 1-cyclopropyl-bugtane-2,3-di- one with the appropriate phenylhydrazine and by separation of the desired diketone monophenylhydrazone from the resulting mixture of phenylhydrazones. Halogenation then affords the compounds of Formula I.

The new 1'-formyl-1'-halobenzeneazomethanes of Formula I wherein R is alkoxy and R' is alkyl are readily prepared by halogenation of the phenylhydrazone of the appropriate α-keto esters, e.g., methyl pyruvate (2,4,6-trichlorophenyl)-hydrazone.

The vigorous halogenation of the starting phenylhydrazones to produce 1'-formyl-1'-halobenzeneazomethanes according to Formula I is effected in an organic solvent medium. Representative suitable ones are chloroform (preferred), carbon tetrachloride, trichlorofluoromethane, benzene, acetic acid, and the like. The starting compound is dissolved in the solvent medium and the halogenating agent is added. The reaction is conveniently effected at low temperature so that it can be controlled. The reaction vessel is fitted with a condenser, cooled with a mixture of solid carbon dioxide and acetone to allow escape of hydrogen chloride liberated in te reaction but return the unreacted chlorine to the reaction mixture. Illustratively, a direct chlorination reaction can be effected by chilling the solvent medium in a reaction vessel to minus 60° C. (-60°)or to a temperature slightly above the freezing point of the reaction mixture and adding a measured amount of liquified chlorine.

When any initial and rapid halogenation has subsided the reaction mixture is allowed to warm to about 25° C. to complete the reaction and the excess chlorine can be permitted to escape the reaction vessel. The solvent medium can be removed by evaporation to give the desired 1-formyl-1'-halobenzeneazomethane which may be purified by distillation. Alternatively, the desired compound can be recovered from the reaction medium by chromatographic procedures - the colored azo product providing inherent advantage for column separation and recovery. The solid 1'-formyl-1'-halobenzeneazomethanes are purified by conventional recrystallization from suitable solvents, e.g., technical hexane, benzene, ethanol, and the like.

Preparation I

A solution consisting 138 g. (2 moles) sodium nitrite and 300 ml. water was added slowly with stirring to a solution consisting of 214 g. (2.9 moles) m-toluidine, 440 ml. concentrated hydrochloric acid and 1.5 l. water. The solutions had been cooled to 0° C. After addition of the sodium nitrite solution was completed, a solution consisting of 280 g. sodium acetate in about 700 ml. water was added to the reaction mixture. A further solution of 232 g. methyl acetoacetate in 300 ml. methanol was mixed with a cooled solution of 80 g. sodium hydroxide in 500 ml. water and this mixture was added rapidly to the above-described reaction mixture. A red oil separated, and after 10 minutes 750 ml. chloroform was added. The red oil dissolved in te chloroform, and this chloroform solution was withdrawn from a separatory funnel. The separated chloroform solution was washed well with water and dried.

The chloroform was removed by evaporation under reduced pressure to give 265 g. (57% yield) of methyl 2,3-dioxobutyrate-2-(m-tolyl)hydrazone. A portion of te oil was crystallized two times from methanol to give an analytical sample having a melting point of 84° to 86° CC.

Analysis: Calc'd. for $C_{12}H_{14}N_2O_3$: C, 61.52; H, 6.02. Found: C, 61.07; H, 6.02.

Preparation II

A solution consisting of 5 g. (0.021 mole) methyl 2,3-dioxobutyrate-2-(m-tolyl)hydrazone (Preparation I, above) and 50 ml. chloroform was chilled to minus 60° C. (−60°) and 10 ml. chlorine was added. This reaction solution was allowed to warm to 25° C. and the chloroform was removed by evaporation under reduced pressure. The residue that remained was dissolved in hot technical hexane, and the solution was cooled. A precipitate formed. The precipitate was collected on a filter, and the filter cake was recrystallized from technical hexane to give methyl chloroglyoxylate 2-(2,4,6-trichloro-m-tolyl)hydrazone having a melting point at 96° to 98° C.

Analysis: Calc'd. for $C_{10}H_8Cl_4N_2O_2$: C, 36.39; H, 2.44; Cl, 42.98; N, 8.49. Found: C, 36.47; H, 2.56; Cl, 43.14; N, 8.32.

Preparation III

A mixture consisting of 61 g. (0.20 mole) chloroglyoxylic acid (2,4,6-trichlorophenyl)hydrazone, 200 ml. carbon tetrachloride, and 100 ml. thionyl chloride was heated at the reflux temperature ofj 6 ½ hrs. The carbon tetrachloride and thionyl chloride were removed by evaporation under reduced pressure and 50° C. to give 64 g. of an oil. The oil was extracted with technical hexane and the insoluble starting material was removed by filtration. The technical hexane was removed by evaporation under reduced pressure to give chloroglyoxyloyl chloride (2,4,6-trichlorophenyl)hydrazone.

Preparation IV

A solution consisting of 17.0 g. )0.05 mole) chloroglyoxyloyl chloride (2,4,6-trichlorophenyl)hydrazone and 200 ml. ethanol was heated at the reflux temperature for 30 min. This reaction solution was then concentrated to a volume of about 50 ml. and cooled. The solids that separated were recovered on a filter, and the solids on the filter were recrystallized two time from technical hexane to give ethyl chloroglyoxylate 2-(2,4,6-trichlorophenyl)-hydrazone having a melting range at 65° to 73° C.

Analysis: Calc'd. for $C_{10}H_8Cl_4N_2O_2$: C, 36.39; H, 2.44; Cl, 42.98; N, 8.49. Found: C, 36.49; H, 2.89; Cl, 42.93; N, 8.68.

Following the same procedure but separately substituting methanol, isopropyl alcohol, n-butyl alcohol, n-amyl alcohol, n-hexyl alcohol, n-heptyl alcohol, cyclobutanol, cyclopentanol, n-octyl alcohol, cyclohexanol, 4-methylcyclohexanol, cycloheptanol, 2-chloroethanol, 2,2-dichloroethanol, 2,2,2-trichloroethanol, 3-bromo-1-propanol, 3-chloro-2-methyl 1-propanol, 4-fluorobutanol, 1,1,1-trichloro-2-butanol, 3-bromo-2-butanol, 5-fluoro-1-pentanol, and 7-fluoro-1-heptanol for ethanol, there was prepared, methyl chloroglyoxylate 2-(2,4,6-trichlorophenyl)hydrazone, isopropyl-, n-butyl-, n-amyl-, n-hexyl-, n-heptyl-, cyclobutyl-, cyclopentyl-, n-octyl-, cyclohexyl-, 4-methylcyclohexl , cycloheptyl-, 2-chloroethyl-, 2,2-dichloroethyl-, 2,2,2-trichloroethyl-, 3-bromopropyl-, 3-chloro-2-methylpropyl-, 4-fluorobutyl-, 1,1,1-trichloro-sec.butyl-, 3-bromo-sec.butyl-, 5-fluoroamyl-, and 7-fluoroheptyl chloroglyoxylate 2-(2,4,6-trichlorophenyl)- hydrazone, respectively.

EXAMPLE 1

Preparation of 1,1-Dichloro-1-[(4,6-Dichloro-O-tolyl)azo]-2-Propanone

A solution consisting of 27.9 g. (0.1 mole) pyruvoyl chloride (4,6-dichloro-o-tolyl)hydrazone and 200 ml. carbon tetrachloride was stirred thoroughly while 15 ml. chlorine was added. This addition was effected at room temperature by permitting liquified chlorine to vaporized into a reaction vessel fitted with a condenser cooled by solid carbon dioxide. Stirring was continued for 18 hrs. and some of the chlorine escaped after all the solid carbon dioxide had sublimed. Upon removing the carbon tetrachloride by evaporation under reduced pressure, there was obtained 1,1-di- chloro-1-[(4,6-dichloro-o-tolyl)azo]-2-propanone as an orange-red oil.

The product was characterized by an infrared absorption band at 1745 cm.$^{-1}$ (carbonyl), and a strong absorption band at 1575 cm$^{-1}$ (phenylazo).

The nuclear magnetic resonance spectrum showed absorptions at 7.34δ (one aromatic hydrogen, doublet J =2.5Hz), 7.16δ (one aromatic hydrogen, doublet J =2.5Hz), 2.54δ (three hydrogens, singlet) and 2.32δ (three hydrogens, singlet).

It decomposed in methanol containing added morpholine to give phosgene-(4,6-dichloro-o-toly)hydrazone having a melting point of 58° to 60° C.

EXAMPLE 2

Preparation of Ethyl 2-Chloro-2-[(2,4,6-Trichlorophenyl)azo]propionate

Part A. Ethyl pyruvate (2,4,6-trichlorophenyl)hydrazone

A reaction mixture consisting of 12.7 ml. elthyl pyruvate, 21.2 g. (0.10 mole) (2,4,6-trichlorophenyl)hydrazine and 200 ml. benzene was heated at the reflux temperature for 20 min. with a Dean and Stark water trap attached. After 1.8 ml. water had been collected, the reaction mixture was concentrated to a volume of 60 ml. by removing the benzene by evaporation under reduced pressure. The concentrate was poured onto a 50 × 5 cm. column of silica gel, and the chromatogram was developed with benzene until the colored (pale yellow) zone reached the outlet. 100 ml. of eluate was discarded, and the next 200 ml. was saved. The benzene was removed from this 200 ml. fraction by evaporation under reduced pressure and 4.3 g. of syn ethyl pyruvate (2,4,6-trichlorophenyl)hydrazone was obtained. This syn isomer was recrystallized two times from methanol to give the analytical sample having a melting point at 51° to 53° C.

Analysis: Calc'd. for $C_{11}H_{11}Cl_3N_2O_2$: C, 42.67; H, 3.58; Cl, 34.38; N, 9.05. Found: C, 42.58; H, 3.51; Cl, 34.22; N, 8.83.

After discarding the next 200 ml. of eluate that contained mixed isomers, 1200 ml. of eluate was collected that contained, after removal of the benzene by evaporation under reduced pressure, 13.0 g. of anti ethyl pyruvate (2,4,6-trichlorophenyl)hydrazone. The solids were dissolved in hot technical hexane and crystallized therefrom by cooling to obtain crystals having a melting point at 61° to 64° C. A second recrystallization from technical hexane gave 9.8 g. of anti ethyl pyruvate (2,4,6-trichlorophenyl)hydrazone having a melting point at 64° to 68° C.

Analysis: Calc'd. for $C_{11}H_{11}Cl_3N_2O_2$: C, 42.67; H, 3.58; Cl, 34.38; N, 9.05. Found: C, 42.89; H, 3.71; Cl, 34.52; N, 8.96.

Part B. Ethyl 2-chloro-2-[(2,4,6-trichlorophenyl)azo]propionate

A solution consisting of 9.0 g. ethyl pyruvate (2,4,6-trichlorophenyl)hydrazone (mixed isomers) and 100 ml. carbon tetrachloride was chilled to minus 10° (−10°) C. and 5 ml. chlorine gas was added. After allowing the reaction mixture to warm up to about 25° C., the carbon tetrachloride was removed by evaporation under reduced pressure. The oily residue that remained was dissolved in a mixture of benzene and technical hexane (1 part of benzene to 4 parts of the latter). This solution was poured onto a 50 cm. × 5 cm. column of silica gel and the chromatogram was developed with the solvent mixture. The first portion of eluate was discarded and the fractions containing the orange-red azo compound were saved. After removal of the solvents by evaporation at 100° C. and 10 mm. mercury pressure 6.9 g. ethyl 2-chloro-2-[(2,4,6-trichlorophenyl)azo]propionate was obtained.

Analysis: Calc'd. for $C_{11}H_{10}Cl_4N_2O_2$: C, 38.40; H, 2.93; Cl, 41.22; N, 8.14. Found: C, 39.66; H, 3.23; Cl, 41.23; N, 7.93.

In a separate experiment the product was further purified by distillation under reduced pressure and had a boiling point of 155° C. at 0.05 mm. mercury pressure.

Analysis: Calc'd. for $C_{11}H_{10}Cl_4N_2O_2$: C, 38.40; H, 2.93, Cl, 41.22; N, 8.14. Found: C, 38.34; H, 3.01; Cl, 41.33; N, 8.31.

Following the same procedure but substituting methyl pyruvate (2,4,6-trichlorophenyl)hydrazone for ethyl pyruvate (2,4,6-trichlorophenyl)hyrazone, there was prepared methyl 2-chloro-2-[(2,4,6-trichlorophenyl)azo]propionate.

Analysis: Calc'd. for $C_{10}H_8Cl_4N_2O_2$: C, 36.39; H, 2.44; Cl, 42.98; N, 8.49. Found: C, 37.46; H, 2.93; Cl, 40.43 N, 8.28.

EXAMPLE 3

Preparation of Ethyl 2-Fluoro-2-[(2,4,6-Trichlorophenyl)azo]propionate

A solution consisting of 6.0 g. (0.02 mole) ethyl pyruvate (2,4,6-trichlorophenyl)hydrazone and 100 ml. trichlorofluoromethane was chilled to minus 60° (−60°) C. and about 4 g. of trifluoromethylhypofluorite was slowly added in a bubbling stream while the solution was stirred. This reaction mixture was allowed to warm slowly to room temperature, and was then slowly warmed further to 40° C. The escaping gases were passed through an aqueous solution of sodium iodide. When the volatile components, including the trichlorofluoromethane solvent, had been removed, the residue was dissolved in technical hexane. This solution was poured onto a 50 cm. ×5 cm. column of silica gel and the chromatogram was developed with a mixture of benzene and technical hexane (1 part benzene to 3 parts the latter). The fractions showing presence of the yellow azo compound were collected and combined. After removing the solvents by evaporation at a temperature of 100° C. and reduced pressure (10 mm Hg.), there was obtained 3.2 g. of ethyl 2-fluoro-2-[(2,4,6-trichlorophenyl)azo]propionate.

Analysis: Calc'd. for $C_{11}H_{10}Cl_3FN_2O_2$: C, 40.33; H, 3.08; Cl, 32.47; F, 5.08; N, 8.55. Found: C, 40.76; H, 3.44; Cl, 32.70; N, 8.73.

EXAMPLE 4

Preparation of Ethyl 2-Chloro-2-[(o-Methoxyphenyl)azo]propionate

Part A. Ethyl pyruvate (o-methoxyphenyl)hydrazone

After adding 20 ml. (0.15 mole) ethyl pyruvate to a solution of 26.1 g. (0.15 mole) o-methoxyphenylhydrazine hydrochloride in 200 ml. ethanol, the reaction solution was heated for 5 mins. at about 60° C. After cooling the reaction mixture and diluting with water, a precipitate formed. The solids were collected on a filter and recrystallized from methanol. There was thus obtained 17.8 g. of ethyl pyruvate (o-methoxyphenyl)hydrazone as a mixture of syn and anti isomers (60% and 40%, respectively) having a melting range of 58° to 83° C.

Analysis:

Calc'd. for $C_{12}H_{16}N_2O_3$: C, 61.00; H, 6.83. Found: C, 61.08; H, 7.03.

Part B. Ethyl 2-chloro-2-[(o-methoxyphenyl)azo]propionate

After dissolving 10.4 g. (0.05 mole) of ethyl pyruvate (o-methoxyphenyl)hydrazone (prepared in Part A, above) in 100 ml. chloroform a solution of 12 ml. (0.1 mole) tert.-butyl hypochlorite in chloroform was added slowly. An exothermic reaction occurred, and after 30 min. the chloroform was removed by evaporation at 100° C. and 10 mm. Hg. pressure. The residual oil thus obtained was a mixture of ethyl 2-chloro-2-[(o-methoxyphenyl)azo]propionate (70%) and ethyl 2-chloro-2-[(o-methoxychlorophenyl)azo]propionate (30%). That a mixture of the above chemicals had been obtained was evident from the nuclear magnetic resonance spectrum which showed that the product had 3.7 aromatic hydrogen atoms. The analytical data also indicated the presence of two compounds.

Analysis: Calc'd. for $C_{12}H_{15}ClN_2O_3$: C, 53.24; H, 5.59; Cl, 13.10; N, 10.35. Calc'd. for $C_{12}H_{16}Cl_2N_2O_3$: C, 46.92; H, 5.25; Cl, b 23.09; N, 9.12. Found for the chlorination product: C, 50.31; H, 5.42; Cl, 17.71; N, 10.19.

The two compounds were unstable to chromatography on silica gel, but could be separated by vapor phase chromatography using a column (45 cm. × 3 mm. I.D.) of 3% QF-1 on 100 to 120 mesh Gas-Chrom Q maintained at a temperature of 132° C. The sample (1 μ of a solution containing 2 mg. compound per ml. of chloroform) was injected on the column using a helium carrier gas (flow rate 85 ml. per minute) and the componds were detected using a hydrogen flame ionization detector. Using these conditions ethyl 2-chloro-2-[(o-methoxyphenyl)azo]propionate had a retention time of 1.2 minutes and ethyl 2-chloro-2-[(o-methoxychlorophenyl)-azo]propionate a retention time of 2.5 min.

Following the same procedure, but substituting ethyl pyruvate (p-tolyl)hydrazone there was obtained an oil that contained a mixture of ethyl 2-chloro-2-[(p-tolyl)azo]propionate and ethyl 2-chloro-2-[(chloro-p-tolyl)azo]propionate.

Analysis: Calc'd. for $C_{12}H_{15}ClN_2O_2$: C, 56.58; H, 5.94; Cl, 13.92; N, 11.00 Calc'd. for $C_{12}H_{14}Cl_2N_2O_2$: C, 49.84; H, 4,88; Cl, 24.32; N, 9.69. Found: C, 55.55; H, 5.36; Cl, 16.44; N, 10.89.

Following the same procedure but substituting ethyl pyruvate phenylhydrazone there was obtained an oil that contained a mixture of ethyl 2-chloro-2-(phenylazo)propionate and ethyl 2-chloro-2-[(p-chlorophenyl)azo]propionate.

Analysis: Calc'd. for $C_{11}H_{13}ClN_2O_2$: C, 54.89; H, 5.44; Cl, 14.73; N, 11.64. Calc'd. for $C_{11}H_{12}Cl_2N_2O_2$: C, 48.37; H, 4.43; Cl, 25.96; N, 10.26. Found: C, 48.87; H, 4.33; Cl, 25.23; N, 10.19.

Following the same procedure but substituting ethyl pyruvate (2,5-dichlorophenyl)hydrazone there was prepared ethyl 2-chloro-2-[(2,5-dichlorophenyl)azo]-propionate.

Analysis: Calc'd. for $C_{11}H_{11}Cl_3N_2O_2$: C, 42.67; H, 3.58; Cl, 34.36; N, 9.05. Found: C, 40.10; H, 3.19; Cl, 39.46; N, 8.12.

EXAMPLE 5

Preparation of Ethyl 2-Chloro-2-[(2,4,6-Trichlorophenyl)azo]butyrate

Part A. Ethyl 2-oxobutyrate 2-(2,4,6-trichlorophenyl)hydrazone

A reaction mixture consisting of 11 g. (0.085 mole) ethyl 2-oxobutyrate, 17 g. (0.077 mole) (2,4,6-trichlorophenyl)hydrazine, and 200 ml. benzene was heated at the reflux temperature with a Dean and Stark water trap attached to the reaction vessel. When all the water produced by the reaction had been removed, the benzene was removed by evaporation under reduced pressure. The oily residue that remained was dissolved in hot technical hexane, and this solution was allowed to cool. Crystals of the desired product separated and 15.2 g. were recovered. Recrystallization from methanol gave an analytical sample of ethyl 2-oxobutyrate 2-(2,4,6-trichlorophenyl)hydrazone having a melting point at 97° to 99° C.

Analysis:
Calc'd. for $C_{12}H_{13}Cl_3N_2O_2$: C, 44.54; H, 4.05; Cl, 32.87; N, 8.66. Found: C, 44.44; H, 4.14; Cl 32.82; N, 8.74.

Part B. Ethyl 2-chloro-2-[(2,4,6-trichlorophenyl)azo]-butyrate

A solution consisting of 10 g. (0.031 mole) ethyl 2-oxobutyrate 2-(2,4,6-trichlorophenyl)hydrazone (prepared in Part A, above) and 100 ml. chloroform was chilled to minus 40° C. (−40° ) and 5 ml. chlorine was added. The reaction mixture was maintained at −40° C. for one hr., and then the chloroform was removed by evaporation under reduced pressure. The residual oil thus obtained was purified by column chromatography on silica gel using benzene as the solvent. The fractions containing the orange-red azo compound were pooled and the solvent was removed by evaporation at 100° C. and a pressure of 10 mm Hg. to give 7.4 g. of ethyl 2-chloro-2-[(2,4,6-trichlorophenyl)azo]butyrate as an oil.

Analysis: Calc'd. for $C_{12}H_{12}Cl_4N_2O_2$: C, 40.25; H, 3.38; Cl, 39.61; N, 7.83. Found: C, 40.80; H, 3.25; Cl, 39.53; N, 8.12.

EXAMPLE 6

Preparation of Methyl Chlorophenyl [(2,4,6-Trichlorophenyl)azo]acetate

Part A. Methyl phenylglyoxylate (2,4,6-trichlorophenyl)hydrazone

A reaction mixture consisting of 16.4 g. (0.1 mole) methyl benzoylformate, 21.7 g. (0.1 mole) (2,4,6-trichlorophenyl)hydrazine, and 100 ml. benzene was heated at the reflux temperature for 1 hr. The water produced by the reaction (1.7 ml.) was removed by a Dean and Stark trap. When the reaction was completed, the benzene was removed by evaporation under reduced pressure, and the remaining oil was dissolved in 50 ml. hot technical hexane. After cooling, solids separated and were recovered on a filter. The solids on the filter were recrystallized from ethyl acetate to give 20.1 g. methyl phenylglyoxylate (2,4,6-trichlorophenyl)-hydrazone as a mixture of isomers melting in the temperature range 111° to 123° C.

Analysis: Calc'd. for $C_{15}H_{11}Cl_3N_2O_2$: C, 50.37; H, 3.10; Cl, 29.74; N, 7.84. Found: C, 50.36; H, 3.13; Cl, 29.87; N, 7.79.

Part B. Methyl chlorophenyl [(2,4,6-trichlorophenyl)azo]-acetate

A solution consisting of 14.0 g. (0.04 mole) methyl phenylglyoxylate (2,4,6-trichlorophenyl)hydrazone and 200 ml. chloroform was chilled to minus 30° C. and 5 ml. chlorine was added. This reaction mixture was stirred continuously for 30 min. at minus 10° C., after which the chloroform and excess chlorine were removed by evaporation under reduced pressure. There was thus obtained 19.05 g. of an oily residue that was dissolved in warm technical hexane. Solids separated when the solution was cooled, and these solids were recrystallized from technical hexane to give 10.4 g. of methyl chlorophenyl [(2,4,6-trichlorophenyl)-azo]acetate having a melting point at 56° to 58° C.

Analysis: Calc'd for $C_{15}H_{10}Cl_4N_2O_2$: C, 45.95; H, 2.57; Cl, 36.17; N, 7.15. Found: C, 45.83; H, 2.48; Cl, 36.33; N, 7.33.

EXAMPLE 7

Preparation of Methyl Dichloro-[(2,4,6-Trichloro-m-tolyl)azo]acetate

A solution consisting of 100 g. (0.43 mole) methyl 2,3-dioxobytyrate-2-(m-tolyl)hydrazone (Preparation 1, anti) and 400 ml. chloroform was chilled to minus 60° C. (−60° ) and 200 ml. chlorine was added while the reaction mixture was kept stirred. The reaction progressed rapidly to completion, but the reaction mixture was stirred at 25° C. for 18 hrs. The chloroform was then removed by evaporation under reduced pressure to give 167 g. of an oily residue. A 102 g. portion of the oil was crystallized from methanol and 57 g. of methyl dichloro [(2,4,6-trichloro-m-tolyl)azo]-acetate having a melting point at 44° to 46° C. was recovered. Recrystallization from petroleum ether gave the analytical sample having a melting point at 44° to 46° C.

Analysis: Calc'd. for $C_{10}H_7Cl_5N_2O_2$: C, 32.95; H, 1.94; Cl, 48.64; N, 7.69. Found: C, 33.21; H, 2.00; Cl, 48.09; N, 7.26.

EXAMPLE 8

Preparation of Methyl Dichloro[(2,6-Dichlorop-tolyl)azo]acetate

A solution consisting of 60 g. (0.25 mole) methyl 2,3-dioxobutyrate 2-(p-tolyl)hydrazone and 500 ml. chloroform was chilled to minus 60° C. (−60°) and 100 ml. chlorine was added. The reaction mixture was allowed to warm to about 25° C. and stirred for 18 hrs. while a condenser chilled with solid carbon dioxide prevented escape of chlorine. The chloroform was then removed by evaporation under reduced pressure. The residue thus obtained was dissolved in a solvent mixture of benzene and technical hexane (1 part:1 part) and poured onto a column of silica gel 100 cm. × 7 cm. The chromatogram was developed with the solvent mixture and the portion containing a yellow adsorbate was saved. After removing the solvents by evaporation under reduced pressure, the residue was dissolved in methanol. Upon cooling the methanolic solution, a yellow precipitate formed that was recovered on a filter. The filter cake was recrystallized from petroleum ether to give 4.7 g. of methyl dichloro[2,6-dichloro-p-tolyl)azo]acetate having a melting point at 48° to 51° C.

Analysis: Calc'd. for $C_{10}H_8Cl_4N_2O_2$: C, 36.39; H, 2.44; Cl, 42.98; N, 8.48. Found: C, 36.39; H, 2.68; Cl, 42.69; N, 8.48.

EXAMPLE 9

Preparation of Ethyl Dichloro [(2,4-dichlorophenyl)azo]acetate

A solution consisting of 5.0 g. (0.17 mole) ethyl chloroglyoxylate (2,4-dichlorophenyl)hydrazone and 50 ml. chloroform was added with stirring to a solution of 5.0 g. calcium hypochlorite and 50 ml. water. This two phase reaction mixture was stirred vigorously for an additional 18 hrs. The chloroform layer was separated, washed with water, and dried over anhydrous sodium sulfate. The chloroform was removed by evaporation under reduced pressure. The residual oil thus obtained was dissolved in benzene and the solution was poured onto a column of silica gel 100 cm. by 7 cm. The chromatogram was developed with benzene and the compound ethyl dichloro[(2,4-dichlorophenyl-)azo]acetate was recovered from the eluate by evaporating the solvent at 100° C. and 10 mm Hg. pressure.

Analysis: Calc'd. for $C_{10}H_8Cl_4N_2O_2$: C, 36.39; H, 2.44; Cl, 42.98; N, 8.49. Found: C, 36.52; H, 2.59; Cl, 45.18; N, 8.17.

EXAMPLE 10

Preparation of Ethyl Dichloro[(2,4,6-Trichlorophenyl)azo]acetate

A solution consisting of 9.0 g. (0.027 mole) ethyl chloroglyoxylate (2,4,6-trichlorophenyl)hydrazone and 70 ml. chloroform was mixed with a solution of 12.0 g. calcium hypochlorite in 70 ml. water. Stirring was continued for 2 days. The chloroform layer was separated, washed with water, and dried over anhydrous sodium sulfate. The dried solution was then concentrated to a gum by evaporating the chloroform. The residual gum was dissolved in a mixture of benzene and technical hexane (1 part:1 part), and the solution was poured onto a column of silica gel 100 cm. × 7 cm. Development of a chromatogram with the solvent mixture produced a yellow zone which was finally eluted from the column. This eluent fraction was collected, and the solvents were removed by evaporation under reduced pressure. The orange liquid that remained was ethyl dichloro[(2,4,6-trichlorophenyl)azo]acetate.

Analysis: Calc'd for $C_{10}H_7Cl_5N_2O_2$: C, 32.95; H, 1.94; Cl, 48.64; N, 7.96. Found: C, 33.78; H, 2.13; Cl, 49.77; N, 7.99.

Following the same procedure but substituting methyl-, isopropyl- and butyl-chloroglyoxylate-2-(2,4,6-trichlorophenyl)hydrazone for ethyl chloroglyoxylate 2-(2,4,6-trichlorophenyl)hydrazone there were prepared methyl dichloro[(2,4,6-trichlorophenyl)azo]acetate, Analysis: Calc'd. for $C_9H_5Cl_5N_2O_2$: C, 30.85; H, 1.44; Cl, 50.59; N, 7.99. Found: C, 31.50; H, 1.65; Cl, 50.89; N, 7.90.

isopropyl dichloro[(2,4,6-trichlorophenyl)azo]acetate,

Analysis: Calc'd. for $C_{11}H_9Cl_5N_2O_2$: C, 34.91; H, 2.40; Cl, 48.64; N, 7.40. Found: C, 34.84; H, 2.48; Cl, 48.30; N, 7.37.

n-butyl dichloro[(2,4,6-trichlorophenyl)azo]acetate,

Analysis: Calc'd. for $C_{12}H_{11}Cl_5N_2O_2$: Cl, 45.17; N, 7.14. Found: Cl, 46.12; N, 7.21.

Following the same procedure but substituting n-amyl-, n-hexyl-, n-heptyl-, cyclobutyl-, cyclopentyl-, n-octyl-, cyclohexyl-, 4-methylcyclohexyl-, cycloheptyl-, 2-chloroethyl-, 2,2-dichloroethyl-, 2,2,2-trichloroethyl-, 3-bromopropyl-, 3-chloro-2-methylpropyl-, 4-fluorobutyl-, 1,1,1-trichloro-sec.butyl-, 3-bromo-sec.-butyl-, 5fluroamyl-, and 7-fluoroheptyl-chloroglyoxylate 2-(2,4,6-trichlorophenyl)-hydrazone for ethyl chloroglyoxylate 2-(2,4,6-trichlorophenyl)hydrazone there is prepared n-amyl dichloro[(2,4,6-trichlorophenyl)azo]acetate,
n-hexyl dichloro[(2,4,6-trichlorophenyl)azo]acetate,
n-heptyl dichloro[(2,4,6-trichlorophenyl)azo]acetate,
cyclobutyl dichloro[(2,4,6-trichlorophenyl)azo]acetate,
cyclopentyl dichloro[(2,4,6-trichlorophenyl)azo]acetate,
n-octyl dichloro[(2,4,6-trichlorophenyl)azo]acetate,
cyclohexyl dichloro[(2,4,6-trichlorphenyl)azo]acetate,
4-methylcyclohexyl dichloro[(2,4,6-trichlorophenyl)-azo]acetate,
cycloheptyl dichloro[(2,4,6-trichlorophenyl)azo]acetate,
2-chloroethyl dichloro[(2,4,6-trichlorophenyl)azo]-acetate,
2,2-dichloroethyl dichloro[(2,4,6-trichlorophenyl)azo]-acetate,
2,2,2-trichloroethyl dichloro[(2,4,6-trichlorophenyl)-azo]acetate,
3-bromopropyl dichloro[(2,4,6-trichlorophenyl)azo]-acetate,
3-chloro-2-methylpropyl dichloro[(2,4,6-trichlorophenyl)azo]acetate,
4-fluorobutyl dichloro[(2,4,6-trichlorophenyl)azo]acetate,
1,1,1-trichloro-2-butyl dichloro[(2,4,6-trichlorophenyl)azo]acetate,
3-bromo-2-butyl dichloro[(2,4,6-trichlorophenyl)azo]-acetate,
5-fluoropentyl dichloro[(2,4,6-trichlorophenyl)azo]-acetate, and 7-fluoroheptyl dichloro[(2,4,6-trichlorophenyl)azo]-acetate.

EXAMPLE 11

Following the procedure of Example 1, but separately substituting
- 2-oxo-butyryl chloride 1-[(4,6-dichloro-o-tolyl)hydrazone],
- 2-oxo-valeryl chloride 1-[(4,6-dichloro-o-tolyl)hydrazone],
- 2-oxo-hexanoyl chloride 1-[(4,6-dichloro-o-tolyl)hydrazone],
- 2-oxo-octanoyl chloride 1-[(4,6-dichloro-o-tolyl)hydrazone],
- 2-oxo-undecyl chloride 1-[(4,6-dichloro-o-tolyl)hydrazone], and
- 2-oxo-3-methylvaleryl chloride 1-[(4,6-dichloro-o-tolyl)hydrazone] for pyruvoyl chloride (4,6-dichloro-o-tolyl)hydrazone, there is prepared
  - 1,1-dichloro-1-[(4,6-dichloro-o-tolyl)azo]-2-butanone,
  - 1,1-dichloro-1-[(4,6-dichloro-o-tolyl)azo]-2-pentanone,
  - 1,1-dichloro-1-[(4,6-dichloro-o-tolyl)azo]-2-hexanone,
  - 1,1-dichloro-1-[(4,6-dichloro-o-tolyl)azo]-2-octanone,
  - 1,1-dichloro-1-[(4,6-dichloro-o-tolyl)azo]-2-undecanone, and
  - 1,1-dichloro-1-[(4,6-dichloro-o-tolyl)azo]-3-methyl-2-pentanone, respectively.

EXAMPLE 12

Following the procedure of Example 1, but separately substituting
- 3-chloropyruvoyl chloride 1-[(4,6-dichloro-o-tolyl)hydrazone],
- 3,3-dichloropyruvoyl chloride 1-[(4,6-dichloro-o-tolyl)hydrazone],
- 3-bromopyruvoyl bromide 1-[(4,6-dichloro-o-tolyl)hydrazone],
- 4,4-dibromo-2-oxo-butyryl chloride 1-[(4,6-dichloroo-tolyl)hydrazone],
- 4,4,4-trifluoro-2-oxo-butyryl chloride 1-[(4,6-dichloro-o-tolyl)hydrazone],
- 3,3,3-trifluoropyruvoyl chloride 1-[(4,6-dichloro-o-tolyl)hydrazone], and
- 3,4-diiodo-2-oxo-undecyl chloride 1-[(4,6-dichloro-o-tolyl)hydrazone] for pyruvoyl chloride 1-[(4,6-dichloro-o-tolyl)hydrazone], there is prepared
  - 1,1,3-trichloro-1-[(4,6-dichloro-o-tolyl)azo]-2-propanone,
  - 1,1,3,3-tetrachloro-1-[(4,6-dichloro-o-tolyl)azo]-2-propane,
  - 1,3-dibromo-1-chloro-1-[(4,6-dichloro-o-tolyl)azo]-2-propanone,
  - 4,4-dibromo-1,1-dichloro-1-[(4,6-dichloro-o-tolyl)-azo]-2-butanone,
  - 1,1-dichloro-4,4,4-trifluoro-1-[(4,6-dichloro-o-tolyl)-azo]-2-butanone,
  - 1,1-dichloro-3,3,3-trifluoro-1-[(4,6-dichloro-o-tolyl)-azo]-2-propanone, and
  - 1,1-dichloro-3,4-diiodo-1-[(4,6-dichloro-o-tolyl)azo]-2-undecanone, respectively.

EXAMPLE 13

Following the procedure of Example 1, but separately substituting
- pyruvoyl chloride 1-[(2,6-dichloro-p-tolyl)hydrazone],
- pyruvoyl chloride 1-[(p-bromophenyl)hydrazone],
- pyruvoyl chloride 1-[(2,5-dichlorophenyl)hydrazone],
- pyruvoyl chloride 1-[(5-iodo-m-tolyl)hydrazone],
- 3-chloropyruvoyl chloride 1-[(2,4,6-trichlorophenyl)hydrazone],
- 3-bromopyruvoyl chloride 1-[(2,4,6-trichlorophenyl)-hydrazone],
- 3-chloropyruvoyl chloride 1-[(6-chloro-α,α,α-trifluoro-m-tolyl)hydrazone], 3,3-dibromopyruvoyl bromide 1-[(2,4-dibromophenyl)-hydrazone],
- 3-iodopyruvoyl chloride 1-[(2,4,6-trichlorophenyl)-hydrazone],
- pyruvoyl chloride 1-[(α,α,α,α',α',α'-hexafluoro-3,5-xylyl)hydrazone],
- pyruvoyl chloride 1-[(4-chloro-2,5-xylyl)hydrazone],
- pyruvoyl chloride 1-[(4,6-dichloro-m-anisyl)hydrazone],
- pyruvoyl chloride 1-[(2-chloro-α,α,α-trifluoro-ptolyl)hydrazone],
- pyruvoyl chloride 1-[(4-chloro-α,α,α-trifluoro-o-tolyl)hydrazone],
- pyruvoyl chloride 1-[(6-bromo-α,α,α-trifluoro-mtolyl)hydrazone],
- pyruvoyl chloride 1-[(p-fluorophenyl)hydrazone],
- pyruvoyl chloride 1-[(o-fluorophenyl)hydrazone], and
- pyruvoyl chloride 1-[(6,α,α,α-tetrafluoro-m-tolyl)-hydrazone] for pyruvoyl chloride 1-[(4,6-dichloro-o-tolyl)-hydrazone], there is prepared
  - 1,1-dichloro-1-[(2,6-dichloro-p-tolyl)azo]-2-propanone,
  - 1,1-dichloro-1-[(4-bromo-2-chlorophenyl)azo]-2-propanone,
  - 1,1-dichloro-1-[(2,4,5-trichlorophenyl)azo]-2-propanone,
  - 1,1-dichloro-1-[(2,4,6-trichloro-5-iodo-m-tolyl)azo]-2-propanone,
  - 1,1,3-trichloro-1-[(2,4,6-trichlorphenyl)azo]-2-propanone,
  - 3-bromo-1,1-dichloro-1-[(2,4,6-trichlorophenyl)azo]-2-propanone,
  - 1,1,3-trichloro-1-[(6-chloro-α,α,α-trifluoro-m-tolyl)-azo]-2-propanone,
  - 1,3,3-tribromo-1-chloro-1-[(2,4-dibromophenyl)azo]-2-propanone,
  - 1,1-dichloro-3-iodo-1-[(2,4,6-trichlorophenyl)azo]-2-propanone,
  - 1,1-dichloro-1-[(α,α,α,α',α',α'-hexafluoro-3,5-xylyl)-azo]-2-propanone,
  - 1,1-dichloro-1-[(4,6-dichloro-2,5-xylyl)azo]-2-propanone,
  - 1,1-dichloro-1-[(2,4,6-trichloro-m-anisyl)azo]-2-propanone,
  - 1,1-dichloro-1-[(2-chloro-α,α,α-trifluoro-p-tolyl)-azo]-2-propanone,
  - 1,1-dichloro-1-[(4-chloro-α,α,α-trifluoro-o-tolyl)-azo]-2-propanone,
  - 1,1-dichloro-1-[(6-bromo-α,α,α-trifluoro-m-tolyl)-azo]-2-propanone,
  - 1,1-dichloro-1-[(2,6-dichloro-p-fluoro)azo]-2-propanone,
  - 1,1-dichloro-1-[(4,6-dichloro-o-fluorophenyl)azo]-2-propanone, and 1,1-dichloro-1-[(4-chloro-6, α,α,α-tetrafluoro-m-tolyl)-azo]-2-propanone, respectively.

EXAMPLE 14

Following the procedure of Example 1, but separately substituting cyclopropylglyoxyloyl chloride 1-[(4,6-dichloro-otolyl)hydrazone], cyclobutylglyoxyloyl chloride 1-[4,6-dichloro-otolyl)hydrazone], cyclopentylglyoxyloyl chloride 1-[4,6-dichloro-o-tolyl)hydrazone], cyclohexylgloyoxyloyl chloride 1-[(4,6-dichloro-o-tolyl)hydrazone], cycloheptylglyoxyloyl chloride 1-[(4,6-dichloro-o-tolyl)hydrazone], cyclooctylglyoxyloyl chloride 1-[(4,6-dichloro-o-tolyl)-hydrazone, and 3-methylcyclopentylglyoxyloyl chloride 1-[(4,6-dichloro-o-tolyl)hydrazone]for pyruvoyl chloride 1-[(4,6-dichloro-o-tolyl)hydrazone], there is prepared cyclopropyl dichloro[(4,6-dichloro-o-tolyl)azo]-methyl ketone, cyclobutyl dichloro[(4,6-dichloro-o-tolyl)azo]-methyl ketone, cyclopentyl dichloro[(4,6-dichloro-o-tolyl)azo]-methyl ketone, cyclohexyl dichloro[(4,6-dichloro-o-tolyl)azo]-methyl ketone, cycloheptyl dichloro[(4,6-dichloro-o-tolyl)azo]-methyl ketone, cyclooctyl dichloro[(4,6-dichloro-o-tolyl)azo]-methyl ketone, and 3-methylcyclopentyl dichloro[(4,6-dichloro-o-tolyl)-azo]methyl ketone.

EXAMPLE 15

Following the procedure of Example 5, but separately substituting isopropyl 2-oxobutyrate 2-[(2,4,6-trichlorophenyl)-hydrazone], isobutyl 2-oxobutyrate 2-[(2,4,6-trichlorophenyl)hydrazone], octyl 2-oxobutyrate 2-[(2,4,6-trichlorophenyl)hydrazone], ethyl 2-oxopentanoate 2-[(2,4,6-trichlorophenyl)hydrazone], ethyl 2-oxohexanoate 2-[(2,4,6-trichlorophenyl)hydrazone], and ethyl cyclohexylglyoxylate 2-[(2,4,6-trichlorophenyl)-hydrazone]for ethyl 2-oxobutyrate 2-[(2,4,6-trichlorophenyl)hydrazone] there is prepared isopropyl 2-chloro-2-[(2,4,6-trichlorophenyl)azo]-butyrate, isobutyl 2-chloro-2-[(2,4,6-trichlorophenyl)azo]-butyrate, octyl 2-chloro-2-[(2,4,6-trichlorophenyl)azo]butyrate, ethyl 2-chloro-2-[(2,4,6-trichlorophenyl)azo]pentanoate, ethyl 2-chloro-2-[(2,4,6trichlorophenyl)azo]hexanoate, and ethyl 2-chloro-2-cyclohexyl-2-[(2,4,6-trichlorophenyl)-azo]acetate, respectively.

EXAMPLE 16

Part A.

Following the procedure of Example 2, Part A, but separately substituting propyl pyruvate, isopropyl pyruvate, sec.butyl pyruvate, n-amyl pyruvate, n-hexyl pyruvate, n-heptyl pyruvate, n-octyl pyruvate, and 2,5-dimethylhexyl pyruvate for ethyl pyruvate, there is prepared propyl 2-chloro-2-[(2,4,6-trichlorophenyl)azo]propionate.

isopropyl 2-chloro-2-[(2,4,6-trichlorophenyl)azo]-propionate.

sec.butyl 2-chloro-2[(2,4,6-trichlorophenyl)azo]-propionate, n-amyl 2-chloro-2-[(2,4,6-trichlorophenyl)azo]propionate, n-hexyl 2-chloro-2-[(2,4,6-trichlorophenyl)azo]propionate.

n-heptyl 2-chloro-2-[(2,4,6-trichlorophenyl)azo]-propionate, n-octyl 2-chloro-2-[(2,4,6-trichlorophenyl)azo]propionate, and 2,5-dimethylhexyl 2-chloro-2-[(2,4,6-trichlorophenyl)-azo]propionate, respectively.

The 1'-formyl-1'-halobenzeneazomethanes of this invention (compounds according to Formula 1) are active against both greasy and broad-leafed weeds. Corn is not injured. Some known susceptible weeds include crabgrasses (e.g., *Digitaria sanguanalis* and *Digitaria ischaemum*), yellow foxtail (*Setaria lutescens*), bindweed (*Convolvulus arvensis* L.), Johnsongrass (*Sorghum halepense* (L.) Pers.), buckhorn plantain (*Plantago lanceolate* L.), and curly dock (*Rumex crispus*). Numerous other weeds are also controlled by application of the new compounds.

Having now discovered the herbicidal activity of the 1'-formyl-1'-halobenzeneazomethanes of Formula 1, there are certain classes of these compounds that possess distinguishing qualities and are preferred. Illustratively, the compounds of Formula 1 wherein R is alkoxy, R' is alkyl, X is chlorine, and $(Y)_m$ is 3 halogens are one group of preferred compounds of the invention. Among these compounds, the alkyl 2-chloro-2-[(2,4,6-trichlorophenyl)azo]propionates are particularly preferred, especially ethyl 2-chloro-2[(2,4,6-trichlorophenyl)azo]propionate. Other preferred compounds of the invention include, e.g., ethyl dichloro-[(2,4-dichlorophenyl)azo]acetate and isopropyl dichloro-[(2,4,6-trichlorophenyl)acetate.

The 1'-formyl-1'-halobenzeneazomethanes can be applied singly for control of weeds, but if desired a mixture of the compounds can be used. The compounds can be applied in their pure form, as technical grade compounds, as crude mixtures of a compound or compounds, or as improved agronomic formations. Such improved formulations are characterized by the presence of adjuvants that promote effecitve use of the active ingredient compounds and contribute toward economical practice of the invention. In some situations a solvent might be desirable, in other instances a bodying material such as a pulverulent solid might be desirable. Such liquids and solids for diluting the active compounds are termed carriers. In still other situations wetting or dispersing agents, stickers and spreaders, or even other active ingredients might be desired.

Agronomic formulations in accordance with the objective of the inventions include, for example, solutions, liquid suspensions, emulsions, creams, pastes, wettable powders, dusts, emulsifiable concentrates, granulars and impregnated elastomeric strips, ribbons, or blocks. In general, the active component is preferably in a dispersed or readily dispersible form. Dispersibility promotes thorough and uniform coverage of any objectionable area of weeds so that the desired control is realized.

When selective weed control in a crop area or turf is desired, a non-phytotoxic carrier is preferred. In this way the crop plants or desirable grasses are not injured, but the weeds are selectively killed by the 1′-formyl-1′-halobenzeneazomethane active ingredient. Water is an ubiquitous non-phytotoxic carrier. Certain non-phytotoxic crop oils can be used in small amounts of about 1 gal. per acre. Solids ordinarily employed in herbicidal formulations are not phytotoxic. On the other hand, when total control of vegetation is desired, a phytotoxic carrier can be chosen. Appropriate phytotoxic carriers e.g., highboiling petroleum fractions and tetrachlorethane.

The efficacy of 1′-formyl-1′-halobenzeneazomethanes as herbicides is of high order, and the compounds can be applied at relatively low rates per acre for controlling growth of weed plants, e.g., germinating weed seedlings. Illustratively, the compounds ethyl 2-chloro-2-[(2,4,6-trichlorophenyl)azo]propionate and ethyl 2-chloro-2[(2,4,6-trichlorophenyl)azo]butyrate gave complete or substantially complete suppression of redroot pigweed (*Amaranthus retroflexus L.*) when applied at rates of 6 lbs. and 3 lbs. per acre. Rates of application of about 1 to about 15 lbs. per acre are efficacious under usual conditions, depending upon the particular circumstances such as type of soil, amount of rainfall or irrigation, and the most prevalent susceptible weeds. At the high rates of application, e.g., at 20 to 50 lbs. per acre the compound acts as a soil sterilant.

Illustratively, excellent control of weeds in corn fields has been obtained, without significant damage to the corn plants, using concentrations of 1′-formyl-1′-halobenzeneazomethanes ranging from about 1000 ppm (parts per million) to about 5000 ppm applied at the rates of about 1 lb. to about 3 lbs. per acre. In general, a desired rate of application can be achieved by distributing, over the area to be treated, an aqueous spray formulation in accordance with the invention, containing from about 700 ppm to about 30,000 ppm of active ingredient. It will be understood, of course, that a choice of concentration of active ingredient depends upon the method of application as well as the type of formulation and the degree of herbicidal control desired. In general, concentration is not critical within the range indicated since an effective quantity of active ingredient can be applied to a given area by applying greater quantities of a low concentration than of a higher concentration. The concentration of active ingredient in the dispersible powder and emulsifiable concentrates from which the aqueous spray formulations are prepared can be as high as 99.5% by weight. The concentration of active ingredient in the dust and granular formulations of the invention can vary from about 0.25% to about 80% or more, but advantageously is of the order of 0.50% to 20%.

The granular formulations of this invention are prepared with about 0.25% to about 80%, preferably 0.50% to 20% by weight, of active ingredient and a granular carrier, for example, heat expanded vermiculite, heat expanded perlite, pyrophyllite, or attapulgite. The active ingredient can be dissolved in a volatile solvent such as methylene chloride, acetone, and the like, and sprayed on the granular carrier as it is mixed and tumbled. The granules are then dried. The granular carrier can range in particle size from about 10 to about 60 mesh, preferably about 30 to 60 mesh.

The herbicidal dust compositions of the invention are prepared by intimate admixture of from about 0.25% to about 80% by weight, preferably 0.50% to 20% of the active ingredient with a solid pulverulent carrier which maintains the composition in a dry, free-flowing condition. The herbicidal dusts of the invention can be prepared by admixing the compound with a solid diluent and then milling. Preferably, however, the active ingredient is dissolved in a volatile organic solvent, of the kinds indicated above, and then sprayed on the solid carrier so as to assure thorough distribution. The mixture is then dried and milled to the desired size, e.g., less than about 60 microns.

Solid carriers that can be used in the dust compositions of the invention include the natural clays such as China clay and bentonite, minerals in the natural state such as talc, pyrophyllite, quartz, diatomaceous earth, fuller's earth, chalk, and rock phosphate, and the chemically modified minerals such as washed bentonite, precipitated calcium phosphate, precipitated calcium carbonate, precipitated calcium silicate, and colloidal silica. The solid diluents which can be employed in the compositions also include solid, compounded fertilizers. Such solid compositions can be applied to vegetation in the form of dusts by the use of conventional equipment.

A preferred composition, in accordance with the invention, is a dispersible powder which is prepared by incorporating a surfactant in a dust composition prepared as described above. Such a dispersible powder can be dispersed in water to a desired concentration and applied to vegetation by conventional spray equipment. Conveniently the dispersible powders are formulated with higher concentrations of active ingredient than the dust compositions, for example, up to about 90%, preferably about 10% to 18%. Surfactants useful in preparing such dispersible powder compositions include alkyl sulfates and sulfonates, alkyl aryl sulfonates, sulfosuccinate esters, polyoxyethylene sulfates, polyoxyethylene-sorbitan monolaurate, alkyl aryl polyether sulfates, alkyl aryl polyether alcohols, alkyl naphthalene sulfonates, alkyl quaternary ammonium salts, sulfated fatty acids and esters, sulfated fatty acid amides, glycerol mannitan laurate, polyalkylether condensates of fatty acids, lignin sulfonates, and the like. A preferred class of surfactants includes blends of sulfonated oils and polyalcohol carboxylic acid esters (Emcol H-77), blends of polyoxyethylene ethers and oil-soluble sulfonates (Emcol H-400), blends of alkyl aryl sulfonates and alkylphenoxy polyethoxy ethanols (Tritons X-151, X-161, and X-171), e.g., about equal parts of sodium kerylbenzene sulfonate and isooctylphenoxy polyethoxy ethanol containing about 12 ethoxy groups, and blends of calcium alkyl aryl sulfonates and polyethoxylated vegetable oils (Agrimul $N_4S$). It will be understood, of course, that the sulfate and sulfonate and surfactants suggested above will preferably be used in the form of their soluble salts, for example, their sodium salts. All of these surfactants are capable of reducing the surface tension of water to less than about 40 dynes per centimeter in concentrations of about 1% or less. The dispersible powders can be formulated with a mixture of surfactants of the types indicated if desired.

Anionic and nonionic surfactants are preferred. Appropriate anionic surfactants are the calcium salts of myristyl benzenesulfonic acid and lauryl benzenesulfonic acid. An appropriate nonionic surfactant is the oleate ester of a polyoxyethylene glycol having molecular weight about 350–500. Other surfactants as described by J. McCutcheon, *Soap and Chemical Specialties*, (Dec. 1957) and (Jan., Feb., March, and April, 1958) are useful.

A suitable dispersible powder formulation is obtained by blending and milling 235 lbs. of Georgia Clay, 5.5 lbs. of isooctylphenoxy polyethoxy ethanol (Triton X-100) as a wetting agent, 9.5 lbs. of a polymerized sodium salt of substituted benzoid long-chain sulfonic acid (Daxad 27) as a dispersing agent, and 250 lbs. of the active ingredient. The resulting formulation has the following percentage composition (parts herein are by weight unless otherwise specified).

| | |
|---|---|
| Active ingredient | 50 % |
| Isooctylphenoxy polyethoxy ethanol | 1.1% |
| Polymerized sodium salt of substituted benzoid long-chain sulfonic acid | 1.9% |
| Georgia Clay | 47 % |

This formulation, when dispered in water at the rate of 10 lbs. per 100 gals., gives a spray formulation containing about 0.6% (6000 ppm) active ingredient which can be applied to soil, plant growth media, growing plants, e.g., turf at the rate of 40 gals. per acre to give a total application of active ingredients of 2 lbs. per acre.

The compounds of this invention can be applied to soil, plants, plant growth media, growing plants, e.g., turf in aqueous sprays without a solid carrier. However, since the compounds themselves are relatively insoluble in water they are preferably dissolved in a suitable inert organic solvent carrier. Advantageously, the solvent carrier is immiscible with water so that an emulsion of the solvent carrier in water can be prepared. If, for example, a water-miscible solvent carrier such as acetone is used the solvent carrier will dissolve in the water and any excess according to Formula I will be thrown out of solution. In am emulsion, the solvent phase is dispersed in the water phase and the active ingredient is held in solution in the dispersed phase. In this way, uniform distribution of active ingredient with an aqueous spray can be achieved.

A solvent carrier in which the compounds are highly soluble is desirable so that relatively high concentrations of active ingredient can be obtained. Sometimes, one or more solvent carriers with or without a cosolvent can be used in order to obtain concentrated solutions of the active ingredient, the main consideration being to employ a water-immiscible solvent for the active ingredient that will hold the compound in solution over the range of concentrations useful for preventing germination of undesired seeds and controlling growth of plants.

The emulsifiable concentrates of the invention are prepared by dissolving the active ingredient and a surfactant in a substantially water-immiscible solvent carrier (i.e., a solvent carrier which is soluble in water to the extent of less than 2.5% by volume at temperatures of the order of 20° to 30° C.), for example, cyclohexanone, methyl propyl ketone, summer oils, ethylene dichloride, aromatic hydrocarbons such as benzene, toluene, and xylene, and highboiling petroleum hydrocarbons such as heavy aromatic naphtha kerosene, diesel oil, and the like. If desired, a cosolvent such as methyl ethyl ketone, acetone, and the like can be included with the solvent carrier in order to enhance the solubility of the active ingredient. Aqueous emulsions are then prepared by mixing with water to give any desired concentration of active ingredient. The surfactants which can be employed in the aqueous emulsions of the invention are those types noted above. Mixtures of surfactants can be employed if desired.

Advantageously, the concentration of active ingredient in the emulsifiable concentrates can range from about 5% to about 50% by weight, preferably from about 10% to 40%. A concentrate comprising 20% (by weight) of the compound dissolved in a water-immiscible solvent of the kind noted above can be admixed with an aqueous medium in the proportions of 13 ml. of concentrate with 1 gal. of medium to give a mixture containing 700 parts of active ingredient per million parts of liquid carrier. Similarly, 1 qt. of a 20% concentrate mixed with 40 gals. of water provides about 1200 ppm of active ingredient. In the same manner, more concentrated solutions of active ingredient can be prepared.

The concentrate compositions of the invention which are intended for use in the form of aqueous dispersions or emulsions can also comprise a humectant, that is to say, an agent which will delay the drying of the composition in contact with material to which it has been applied. Suitable humectants include solubilized lignins, such as calcium lignosulfonate, and the like.

Further in accordance with this invention, certain formulations of 1'-formyl-1'-halobenzeneazomethanes with oil are particularly efficacious, and herbicidal action of the compound is improved. A petroleum oil having a viscosity rating in the range of 70–100 secs. (Saybolt) is satisfactory. Such nonphytotoxic crop oils are beneficial when used at the rate of about 1 to 2 gals. per acre. They seem to promote penetration of the herbicide into the weeds or perhaps predispose the weed plant surface to penetration.

Advantageously, a 50% wettable powder of the herbicidal active ingredient is mixed with about 38 gals. water and 2 gals. oil for spray application. Alternatively, about 2 gals. oil and a 50% wettable powder are premixed and then dispersed in about 38 gals. water for spray application. In field tests, oil formulations of the foregoing type have given improved herbicidal action.

The rates of application to soils, plant growth media, growing plants, e.g., turf to be protected from noxious weeds will depend upon the species of vegetation to be controlled, the presence or absence of desirable species, the season of year at which treatment is undertaken, and the method and efficiency of application. In general, selective herbicidal activity is obtained when the active compounds are applied at the rate of about 1.0 to about 15 lbs. per acre, preferably at the rate of about 1.0 to about 8 lbs. per acre.

The formulations containing 1'-formyl-1'-halobenzeneazomethanes can be applied to soil, plant growth media, growing plants, e.g., turf, by conventional methods. For example, an area of soil can be treated prior to or after seeding by spraying wettable powder suspensions, emulsions or solutions from boom-type power sprayers or from hand-operated knapsack sprayers. Dusts can be applied by power dusters, or by hand-operated dusters. Dusts and granular formulations can also be applied at the time of seeding in bands spanning the seeded rows.

The following examples are illustrative of the process and products of the present invention, but are not to be construed as limiting.

EXAMPLE 17

A dispersible powder concentrate having the following percentage composition:

| | |
|---|---|
| alkyl dichloro[(2,4,6-trichloro-m-tolyl)azo]-acetate | 45.8% |
| Polymerized sodium salt of substituted benzoid long-chain sulfonic acid (Daxad 27) | 9.2% |
| Kaolinite | 45.0% | was prepared by mixing 250 g. of methyl dichloro[(2,4,6-trichloro-m-olyl)azo]acetate, 50 g. of a polymerized sodium salt of substituted benzoid long-chain sulfonic acid (Daxad 27), and 245 g. of kaolinite. The mixture was milled to a particle size averaging 5 to 30 microns. It was suspended in 10 gals. of water, giving an aqueous spray containing about 6500 parts per million of active ingredient.

EXAMPLE 18

A fine granular formulation having the following percentage composition:

| | |
|---|---|
| alkyl dichloro[(2,4-dichlorophenyl)azo]acetate | 3.7% |
| Vermiculite (30/60 mesh) | 96.3% | was prepared by spraying a solution of 220 g. of ethyl dichloro[(2,4-dichlorophenyl)azo]acetate in 1000 ml. of methylene chloride onto 5780 g. of vermiculite (30 to 60 mesh) while the vermiculite was being tumbled and stirred so as to assure even distribution. The methylene chloride was then evaporated, leaving the active compound adsorbed on the vermiculite, and the vermiculite was pulverized.

EXAMPLE 19

An emulsifiable concentrate having the following percentage composition:

| | |
|---|---|
| Alkyl dichloro[(2,4,6-trichlorophenyl)azo]acetate | 15.0% |
| Technical alkyl naphthalene boiling at 238° to 293° C. (Velsicol AR50) | 19.7% |
| Xylene | 17.4% |
| Acetone | 17.4% |
| Ethylene dichloride | 25.4% |
| Blend of alkyl aryl sulfonates and alkylphenoxy polyethoxy ethanols-(Triton X-151) | 5.1% | was prepared by mixing 15.0 lbs. of isopropyl dichloro[(2,4,6-trichlorophenyl)azo]acetate, 19.7 lbs. of Velsicol AR50, 17.4 lbs. of xylene, 17.4 lbs. of acetone, 25.4 lbs. of ethylene dichloride, and 5.1 lbs. of Triton X-151.

6.67 lbs. of the concentrate mixed with 10 gals. of water gave a spray emulsion containing about 11,000 ppm of active ingredient.

EXAMPLE 20

An emulsifiable concentrate having the following percentage composition:

| | |
|---|---|
| ethyl 2-chloro-2-[(2,4,6-trichlorophenyl)azo]propionate | 40.0% |
| Technical alkyl naphthalene boiling at 238° to 293° C. (Velsicol AR50) | 13.7% |
| Xylene | 12.3% |
| Acetone | 11.3% |
| Ethylene dichloride | 17.7% |
| Blend of alkyl aryl sulfonates and alkylphenoxy polyethoxy ethanols (Triton X-151) | 5.0% | was prepared by mixing 40.0 lbs. of ethyl 2-chloro-2-[(2,4,6-trichlorophenyl)azo]propionate, 20.7 lbs. of Velsicol AR50, 12.3 lbs. of xylene, 11.3 lbs. of acetone, 17.7 lbs. of ethylene dichloride, and 5.0 lbs. of Triton X-151.

1.67 lbs. of the concentrate mixed with 10 gals. of water gave a spray emulsion containing about 8,000 ppm of active ingredient.

EXAMPLE 21

A dispersible powder concentrate having the following percentage composition:

| | |
|---|---|
| methyl dichloro[(2,6-dichloro-p-tolyl)azo]-acetate | 50% |
| Kaolinite clay (finely divided) | 46% |
| Sodium salt of condensed mononaphthalene sulfonic acid (Lomar D) | 4% | was prepared by mixing 50 g. of methyl dichloro[(2,6-dichloro-p-tolyl)azo]acetate, 46 g. of the kaolinite clay, and 4 g. of Lomar D. The mixture was milled to an average particle size of 5 to 30 microns.

EXAMPLE 22

A granular formulation having the following percentage composition:

| | |
|---|---|
| isopropyl dichloro[(2,4,6-trichlorophenyl)azo]acetate | 1% |
| Pyrophyllite (30/60 mesh) | 99% | was prepared by dissolving 1.0 lb. of the isopropyl dichloro[(2,4,6-trichlorophenyl)azo]acetate in 10.0 l. of ethylene dichloride and spraying the solution on 99.0 lbs. of pyrophyllite. The granules were dried and then packaged for use.

EXAMPLE 23

In a test, various amounts of ethyl 2-chloro-2-[(2,4,6-trichlorophenyl)azo]propionate were applied to substantially uniform volumes of a pond compartmented by plastic partitions. Each compartment had 20 sq. ft. of surface area and water depth was 3 ft. Each had about the same association of aquatic plant life, particularly plankton and filamentous algae. The compound was applied by under water injection in amounts calculated to obtain concentrations of 2 ppm, 1 ppm, 0.5 ppm, and 0.25 ppm.

After six weeks, during midsummer, the control of plankton and filamentous algae was observed to be 100%, 90%, 30%, and imperceptible, respectively.

I claim:
1. A compound of the structural formula:

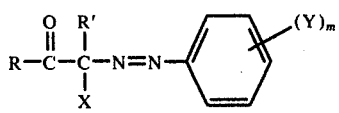

wherein R is alkyl of from 1 to 8 carbon atoms, inclusion; alkoxy of from 1 to 8 carbon atoms, inclusive; haloalkoxy of from 1 to 8 carbon atoms, inclusive; cycloalkyl of from 3 to 8 carbon atoms, inclusive; cycloalkoxy of from 3 to 8 carbon atoms, inclusive; or haloalkyl of from 1 to 8 carbon atoms, inclusive; R' is lower-alkyl of from 1 to 8 carbon atoms, inclusive, phenyl, cycloalkyl of from 3 to 8 carbon atoms, inclusive; or X; X is bromine, chlorine, or fluorine; $m$ is an integer 0 through 5, inclusive, and Y is (independently when m is more than 1) halogen, lower-alkyl of from 1 to 4 carbon atoms, inclusive, lower-alkoxy of from 1 to 4 carbon atoms, inclusive, or halolower-alkyl of from 1 to 4 carbon atoms, inclusive; providing however, that $m$ is 2 whenever R' is X, and that the sum of the carbon atoms in substituents (Y)m is not more than 15.

2. A compound according to claim 1 wherein R is alkyl.

3. A compound according to claim 2 wherein R' is X.

4. A compound according to claim 3 wherein the X's are chlorine.

5. A compound according to claim 4 wherein a Y is halogen.

6. A compound according to claim 5 wherein the halogen is chlorine.

7. A compound according to claim 6 wherein $m$ is 3.

8. The compound according to claim 7, 1,1-dichloro-1-[(4,6-dichloro-o-tolyl)azo]-2-propanone.

9. A compund according to claim 1 wherein R is alkoxy.

10. A compound according to claim 9 wherein R' is alkyl.

11. A compound according to claim 10 wherein X is chlorine or fluorine.

12. A compound according to claim 11 wherein $m$ is 3 or 4.

13. A compound according to claim 12 wherein $m$ is 3 and Y is halogen.

14. A compound according to claim 13 wherein the halogen is chlorine.

15. The compound according to claim 14, ethyl 2-chloro-2-[(2,4,6-trichlorophenyl)azo]propionate.

16. The compound according to claim 14, ethyl 2-chloro-2-[(2,4,6-trichlorophenyl)azo]butyrate.

17. The compounds according to claim 9 wherein R' is a halogen.

18. The compounds according to claim 17 wherein X and R' are chlorine.

19. The compounds according to claim 18 wherein X is halogen.

20. The compounds according to claim 19 wherein Y is chlorine.

21. The compound according to claim 20, ethyl dichloro[(2,4,6-trichlorophenyl)azo]acetate.

22. The compound according to claim 20, ethyl dichloro-[(2,4-dichlorophene)azo]acetate.

23. A compound according to claim 18 wherein (Y)m is halogen and lower-alkyl.

24. A compound according to claim 23 wherein (Y)m is chlorine and lower-alkyl.

25. A compound according to claim 24 wherein lower-alkyl is methyl.

26. The compound according to claim 25, methyl dichloro-[(2,6-dichloro-p-tolyl)azo]acetate.

27. The compound according to claim 25, methyl dichloro-[(2,4,6-trichloro-m-tolyl)azo]acetate.

28. A compound according to claim 9 wherein R' is phenyl.

29. A compound according to claim 28 wherein X is chlorine.

30. A compound according to claim 29 wherein Y is halogen.

31. A compound according to claim 30 wherein Y is chlorine.

32. The compound according to claim 31, methyl chloro-phenyl[(2,4,6-trichlorophenyl)azo]acetate.

33. A compound according to claim 11 wherein R' is methyl.

34. A compound according to claim 33 wherein R is ethoxy.

35. A compound according to claim 34 wherein Y is lower-alkoxy and $m$ is 1.

36. A compound according to claim 35 wherein Y is methoxy.

37. The compound according to claim 36, ethyl 2-chloro-2-[(o-methoxyphenyl)azo]propionate.

38. A compound according to claim 11 wherein X is fluorine.

39. A compound according to claim 38 wherein Y is halogen.

40. A compound according to claim 39 wherein Y is halogen.

41. The compound according to claim 40, ethyl 2-fluoro-2-[(2,4,6-trichlorophenyl)azo]propionate.

* * * * *

UNITED STATES PATENT OFFICE
CERTIFICATE OF CORRECTION

Patent No. 4,006,132    Dated February 1, 1977

Inventor(s) Malcolm W. Moon

It is certified that error appears in the above-identified patent and that said Letters Patent are hereby corrected as shown below:

Column 3, line 28, "clorine" should read --chlorine--; line 50, "cloro" should read --chloro--; line 62, "te" should read --the--; line 63, "hypoclorites" should read --hypochlorites--. Column 4, line 68, "(190)." should read --(1902).--. Column 5, line 21, "pentanetrion" should read --pentanetrione--; line 34, "produce" should read --procedure--; line 49, "bromide" should read --bromine--; line 61, "ae" should read --are--; line 66, "(jphenylhydrazone)" should read --(phenylhydrazone)--. Column 6, line 7, "bugtane" should read --butane--; line 29, "te" should read --the--; line 41, "1-formyl-" should read -- 1'-formyl- --; line 54, "2.9" should read --2.0--; line 65, "te" should read --the--. Column 7, line 4, "te" should read --the--; line 6, "86° CC." should read --86° C.--; line 32, "ofj" should read --for--; line 49, "time" should read --times--; line 68, "methyl-cyclohex1," should read --methylcyclohexyl,--. Column 8, line 29, "7.346" should read --7.34δ--; line 31, "2.546" should read --2.54δ--; line 34, "toly)" should read --tolyl)--. Column 10, line 7, "Cl, 32.70; N, 8.73." should read --Cl, 32.70; F, 5.70; N, 8.73.--; line 47, "Cl,b 23.09" should read --Cl, 23.09--; line 55, "(1 μ of" should read --(1 μl of--. Column 12, line 52, "dioxobytyrate" should read --dioxobutyrate--. Column 13, line 4, "Dichlorop-" should read -- Dichloro-p- --. Column 14, line 31, "5fluroamyl-," should read -- 5-fluoroamyl-, --; line 45, "trichlorphenyl)" should read --trichlorophenyl)--. Column 15, line 43, "dichloroo-" should read -- dichloro-o- --. Column 16, line 23, "ptolyl)" should read --p-tolyl)--; line 27, "mtolyl)" should read --m-tolyl)--; line 43, "trichlorphenyl)" should read --trichlorophenyl)--. Column 17, line 8, "otolyl)" should read --o-tolyl)--; line 9, "otolyl)" should read --o-tolyl)--; line 11, "cyclohexylgloyoxyloyl" should read --cyclohexylglyoxyloyl--.

UNITED STATES PATENT OFFICE
CERTIFICATE OF CORRECTION

Patent No. 4,006,132　　　　　　　　Dated February 1, 1977

Inventor(s) Malcolm W. Moon

It is certified that error appears in the above-identified patent and that said Letters Patent are hereby corrected as shown below:

Column 18, line 9, "trichlorphenyl)" should read --trichlorophenyl)--; line 19, "greasy" should read --grassy--; line 21, "sanguanalis" should read --sanguinalis--; line 25, "lanceolate" should read --lanceolata--. Column 20, line 34, "18%" should read --80%--. Column 23, line 16, "m-olyl)" should read --m-tolyl)--; line 54, "ethanols-(" should read --ethanols (--. Column 24, line 14, "20.7" should read --13.7--. Column 25, lines 10-11, "inclusion;" should read --inclusive;--; line 25, "2 whenever" should read --2 to 5 whenever--. Column 26, line 7, "wherein X" should read --wherein Y--; line 14, "dichlorophene)" should read --dichlorophenyl)--.

Signed and Sealed this

Thirty-first Day of May 1977

[SEAL]

Attest:

RUTH C. MASON
Attesting Officer

C. MARSHALL DANN
Commissioner of Patents and Trademarks